US006752152B2

(12) United States Patent
Gale et al.

(10) Patent No.: US 6,752,152 B2
(45) Date of Patent: Jun. 22, 2004

(54) PNEUMATIC OXYGEN CONSERVING DEVICE

(75) Inventors: Peter P. Gale, Bethlehem, PA (US); Blair J. Hollshwandner, Bethlehem, PA (US); Stephen B. Krentler, Bethlehem, PA (US); Clyde W. Shuman, Allentown, PA (US)

(73) Assignee: Precision Medical, Inc., Northampton, PA (US)

( * ) Notice: Subject to any disclaimer, the term of this patent is extended or adjusted under 35 U.S.C. 154(b) by 153 days.

(21) Appl. No.: 10/040,190

(22) Filed: Oct. 19, 2001

(65) Prior Publication Data

US 2003/0075179 A1 Apr. 24, 2003

(51) Int. Cl.[7] .............................................. A61M 16/00
(52) U.S. Cl. ............................ 128/204.26; 128/205.24
(58) Field of Search .................. 128/200.24, 203.12, 128/203.24, 204.18, 204.21, 204.23, 204.25, 205.18, 205.22, 205.24, 207.12, 207.14–207.18, 204.26

(56) References Cited

U.S. PATENT DOCUMENTS

| 4,054,133 A | * | 10/1977 | Myers .................... 128/204.26 |
| 5,360,000 A | * | 11/1994 | Carter .................... 128/204.26 |
| 5,881,725 A | * | 3/1999 | Hoffman et al. ....... 128/204.26 |
| 6,116,242 A | * | 9/2000 | Frye et al. ............. 128/205.24 |
| 6,364,161 B1 | * | 4/2002 | Pryor ............................ 222/3 |
| 6,425,396 B1 | * | 7/2002 | Adriance et al. ...... 128/204.26 |
| 6,484,721 B1 | * | 11/2002 | Bliss ..................... 128/205.24 |

* cited by examiner

*Primary Examiner*—Glenn K. Dawson
(74) *Attorney, Agent, or Firm*—Richard P. Gilly; Wolf, Block, Schorr and Solis-Cohen

(57) ABSTRACT

A pneumatic oxygen conserving device includes a reservoir of pressurized gas delivered upon inhalation through a single-lumen cannula. Gas flow is interrupted by a series of interconnected passages and chambers, including a check valve which is acted upon by the flow of gas being delivered through the delivery outlet of the device. The device is self regulating to the extent that oxygen pulses of appropriate volume are delivered irrespective of the breathing rate of the user. The device includes a plate with various passages and chambers defined therein in such a way as to reduce the overall length of the device.

27 Claims, 10 Drawing Sheets

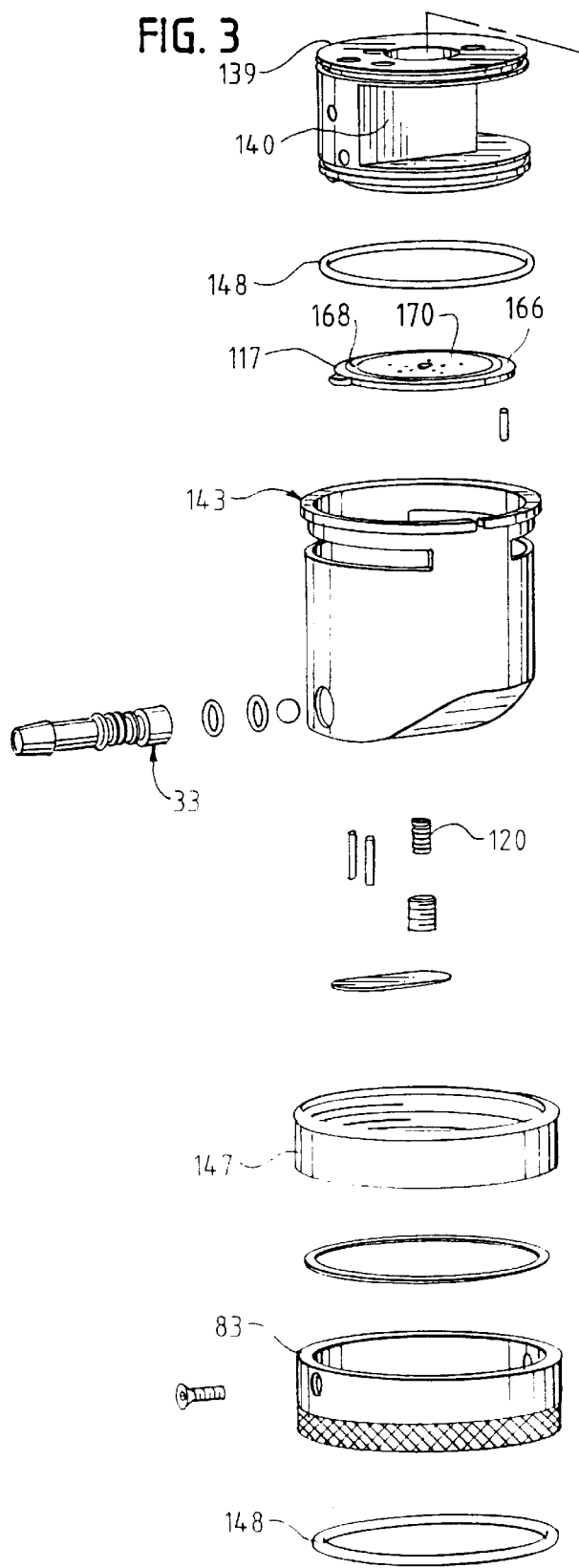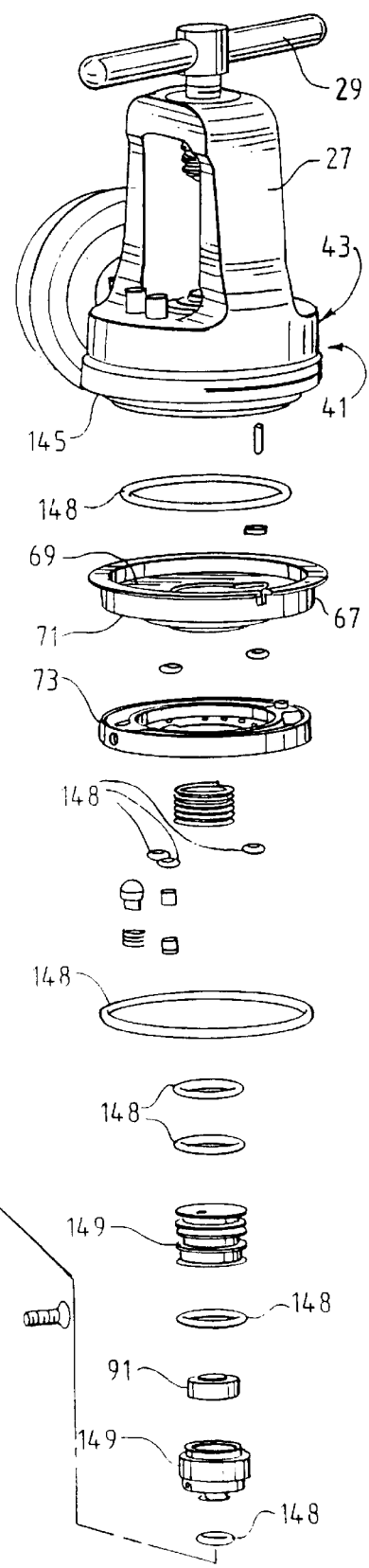
FIG. 3

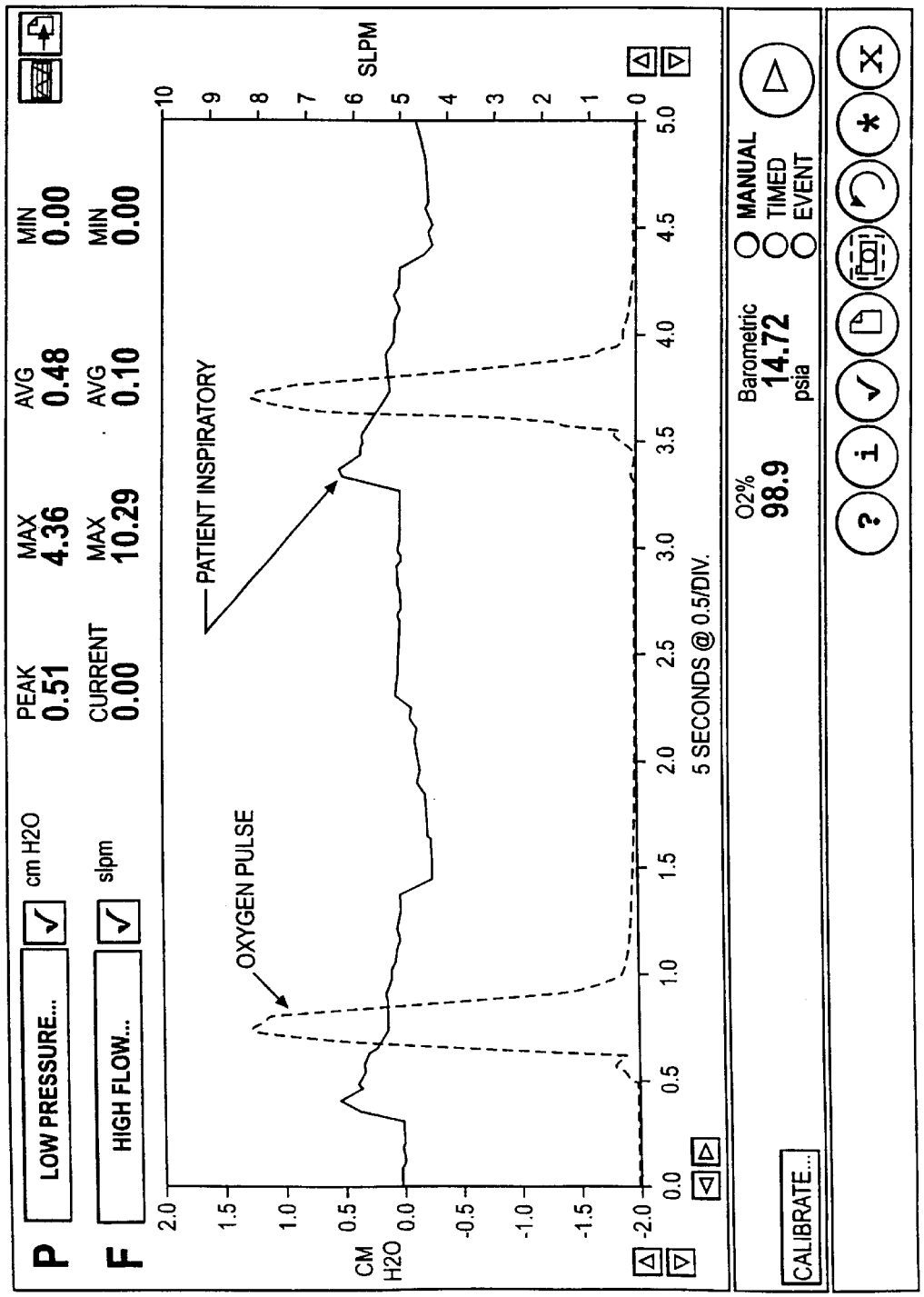

PNEUMATIC OXYGEN CONSERVING DEVICE

FIELD OF THE INVENTION

This invention relates generally to gas delivery systems and, more particularly, to a system for delivering oxygen which includes an oxygen conserving device or oxygen conserver.

BACKGROUND OF THE INVENTION

Gas delivery systems typically include a source of gas, such as oxygen, a regulator for reducing the source pressure of the oxygen to a pressure more suitable for use within the delivery system, and a gas line, typically a cannula, for delivering oxygen from the delivery system to the person. Oxygen delivery systems are used not only in hospitals and health care institutions, but also in home-health care and by ambulatory persons requiring oxygen for any number of reasons. Wherever such oxygen delivery systems are used, it is frequently desirable to increase the life of the oxygen supply. This is especially the case in home-based or ambulatory settings where the supply of oxygen is often an oxygen bottle or other relatively finite oxygen source.

To increase the life of the oxygen supply, oxygen conserving devices, also known as oxygen conservers, are frequently used. These conserving devices generally interrupt the flow of oxygen delivered to the person at regular intervals, thereby reducing the rate of oxygen consumption.

Conservers are generally of two types, those which operate electronically, and those which operate pneumatically. Each of these types suffers from various drawbacks and disadvantages. For example, electronic conservers require a power source, generally a battery, in order to operate, thus necessitating periodic replacement or recharging of the power source.

Electronic oxygen conservers sometimes have further disadvantages related to durability and cost.

Pneumatic oxygen conservers are those which make use of the pressurized gas and its flow within the conserver to intermittently block the delivery of as to the person. Although such pneumatic conservers generally dispense with the need for power sources and complex electronics, they are oftentimes bulkier.

A further disadvantage of pneumatic systems is that they generally require more complex gas lines or cannulas in order to operate. Examples of such pneumatic conservers and their associated dual-lumen cannulas are disclosed in Myers U.S. Pat. No. 5,044,133 and Carter U.S. Pat. No. 5,360,000. One lumen of the cannula is for supplying oxygen to the person wearing the cannula, whereas the other lumen generally connects to a sensing port on the conserver. The pneumatic conserver generally responds to changes in the pressure in the sensing lumen to provide oxygen to the person during inhalation and to interrupt the flow of oxygen to the person in response to exhalation (when oxygen is typically not needed). Unfortunately, dual lumen cannulas are more difficult to obtain, more expensive, bulkier, and generally heavier than the standard, single lumen cannulas used in electronic conservers and many other medical devices.

As a result of these and other drawbacks, pneumatic oxygen conserving devices have not enjoyed widespread use despite certain advantages of such pneumatic conservers over electronic ones.

The various attempts to overcome the drawbacks of pneumatic conservers have had mixed results and have generated their own drawbacks and disadvantages. For example, although the pneumatic oxygen conserver disclosed in Hoffman U.S. Pat. No. 5,881,725, makes use of a single-lumen cannula, the device disclosed therein does not generally deliver oxygen in a manner consistent with the oxygen consumption profiles of a person breathing through a cannula. In other words, it is desirable for oxygen delivery from a conserving device to match a person's needs for oxygen as closely as possible.

There is a need, therefore, for a pneumatic oxygen conserving device which can be used as part of an oxygen delivery system, and which overcomes the disadvantages of current oxygen delivery systems.

SUMMARY OF THE INVENTION

According to one aspect of the invention, a conserving device includes a reservoir which holds a volume of gas for delivery to the person to receive the gas. A delivery system opens and closes an outlet to the reservoir to dispense the gas intermittently. A sensing system detects a pressure drop resulting from inhalation by the person and, as a result of such detection, the sensing system causes the delivery system to open the reservoir outlet. Such opening of the reservoir dispenses the volume of gas from the reservoir and ultimately to the patient. A gas control system is connected to receive gas from the source and from the delivery system the gas control system is connected to the sensing system in such a way that, when the gas control system receives the gas from the delivery system, pressure in the sensing system is increased. The gas control system is further connected to the delivery system to cause the delivery system to close the outlet to the reservoir, in response to increased pressure in the sensing system.

According to another aspect of the present invention, a conserving device includes a reservoir which receives gas from a gas source. A main valve operates to open the reservoir to discharge gas contained therein and to close the reservoir to repressurize it. A pressure line extends from the source of gas to the main valve and biases the main valve toward the closed position. The pressure line also is connected to a sensing valve through a port. The sensing valve is pneumatically connected to a vent to atmosphere and also to a delivery outlet of the device. The delivery outlet is adapted to connect to the gas line. A sensing passage is disposed between the delivery outlet and the sensing valve. When a person inhales, the inhalation is transmitted to the delivery outlet through the gas line. The sensing passage permits air to be drawn from one side of the sensing valve, which then opens the port. When the port opens, gas from the pressure line escapes through the orifice and out the vent to atmosphere. The venting of the gas to atmosphere reduces the biasing of the main valve so that it opens the outlet of the reservoir. Gas discharges from the now open reservoir and exits through the delivery outlet, through the gas line and to the patient. The sensing passage is located relative to the delivery outlet in such a way that some of the gas being delivered passes back through the sensing passage. This returning gas creates sufficient pressure to close the sensing valve, whereupon gas from the pressure line no longer escapes through the vent. Instead the gas from the pressure line closes the main valve to close the reservoir outlet, interrupting delivery of the gas to the patient and permitting repressurizing of the reservoir. In this way, pulses of gas are delivered intermittently and gas is conserved.

In accordance with another aspect of the invention, an orifice plate is included in the device and has a set of vent orifices, a selected one of which is interposed in the vent to atmosphere. In still another version of the invention, the orifice plate includes a set of orifices of varying sizes, each orifice corresponding to a rate of flow of the gas.

In yet another aspect, the invention comprises a pneumatic apparatus for gas delivery through a single-lumen cannula. The apparatus has components housed in a main body, such components including a regulator, a flow-rate selector, a reservoir for receiving gas therein at varying pressures, a main valve movable to open and close the reservoir, a sensing valve responsive to inhalation transmitted through the cannula; a delivery outlet connected to the cannula, and a sensing passage between the delivery outlet and the sensing valve.

The main body includes a plate therein, and the plate is structured to form the reservoir, the main valve, and at least one passage from the main valve.

In one version of the invention, the plate, the regulator, and the flow rate selector are secured to each other along the longitudinal axis of the main body and are substantially cylindrical.

BRIEF DESCRIPTION OF THE DRAWINGS

The invention will be better understood by reference to the attached drawing. It is understood that the drawing is for illustrative purposes only and is not necessarily drawn to scale. In fact, certain features of the drawing are shown in more detail for purposes of explanation and clarification. In the drawing:

FIG. 3 is an exploded perspective view of the conserving device of FIG. 2;

FIG. 14 is a graph of the operation of the device according to the present invention.

DETAILED DESCRIPTION OF THE PREFERRED EMBODIMENTS

Figure 1:
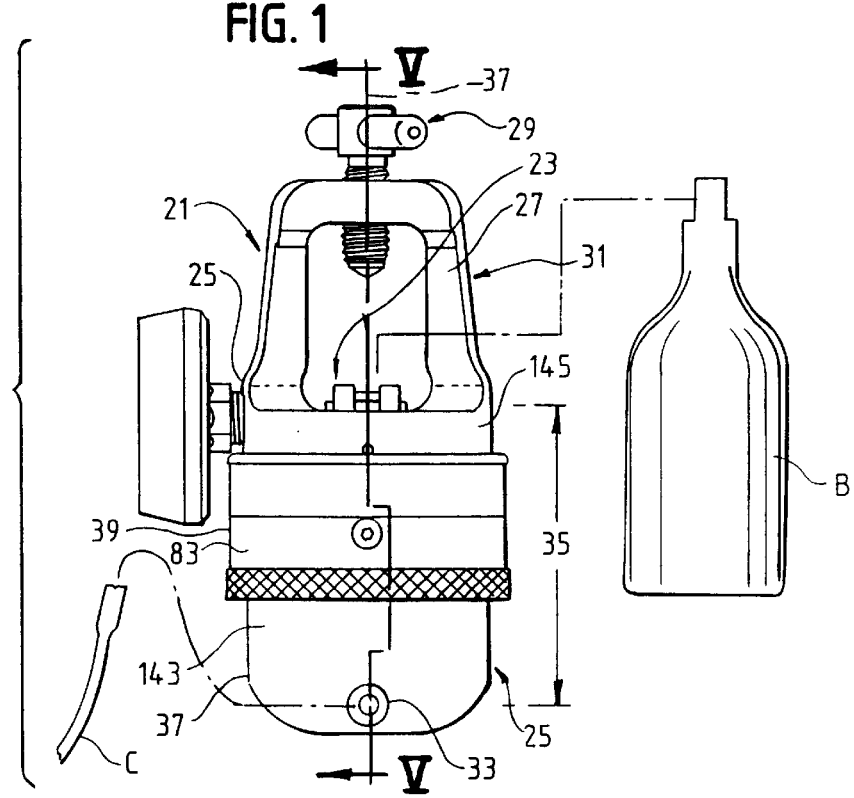
FIG. 1 a side elevational and partly schematic view of an apparatus for delivering oxygen according to the present invention.

Referring now generally to FIG. 1, an apparatus 19 for delivery of oxygen includes an oxygen conserving device or conserver 21 which is pneumatic in design, that is, it makes use of pressurized gas to operate. Conserving device or conserver 21 is connected to gas source B in order to deliver gas to the person intermittently. Oxygen conserving device 21 has the advantage of being usable with any of a variety of standard, single-lumen cannulas, such as that shown by reference numeral C.

Oxygen conserving device 21 has a regulator inlet 23 defined at a suitable location in housing 25 of conserving device 21, preferably toward one of the ends thereof. Inlet 23 is adapted to connect to any of a variety of gas sources, such as bottle of oxygen B under a predetermined pressure. Conserving device 21 includes suitable means for connecting or securing gas source B pneumatically to regulator inlet 23. In this case, such securing means comprises a yoke 27 with a manually adjustable locking handle 29.

Pressurized gas, preferably oxygen, flows from gas source B into regulator inlet 23 and through main body 31 of the conserving device 21. During such travel the gas is acted upon by various valves, passages and other components to be described subsequently. The gas ultimately exits delivery outlet 33 in pulses which are optimally sized and optimally timed, thereby conserving oxygen while supplying such oxygen in the amounts and intervals required by the person receiving oxygen.

Figure 2:
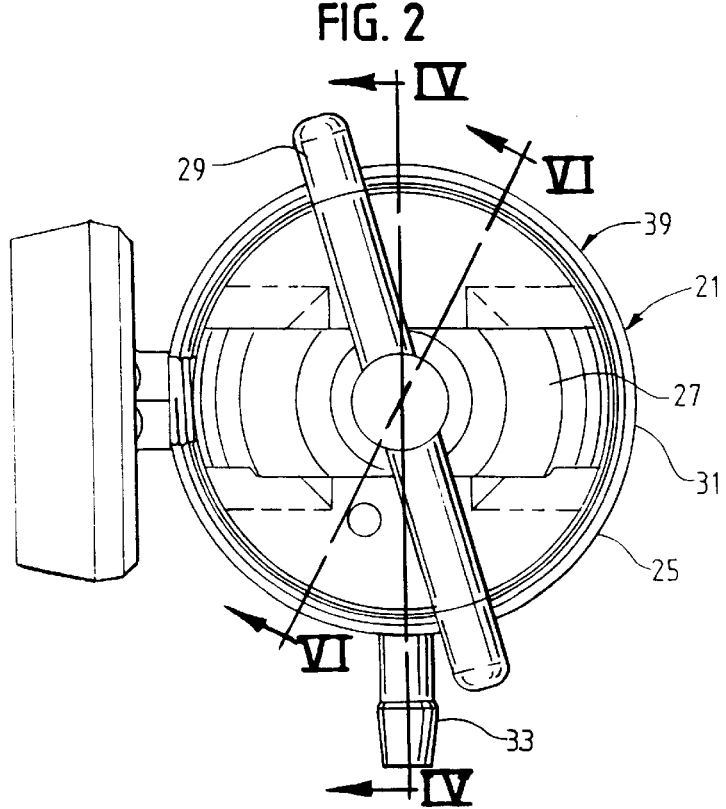
FIG. 2 is a top plan view of the oxygen conserving device of the apparatus shown in FIG. 1.
Figure 4:
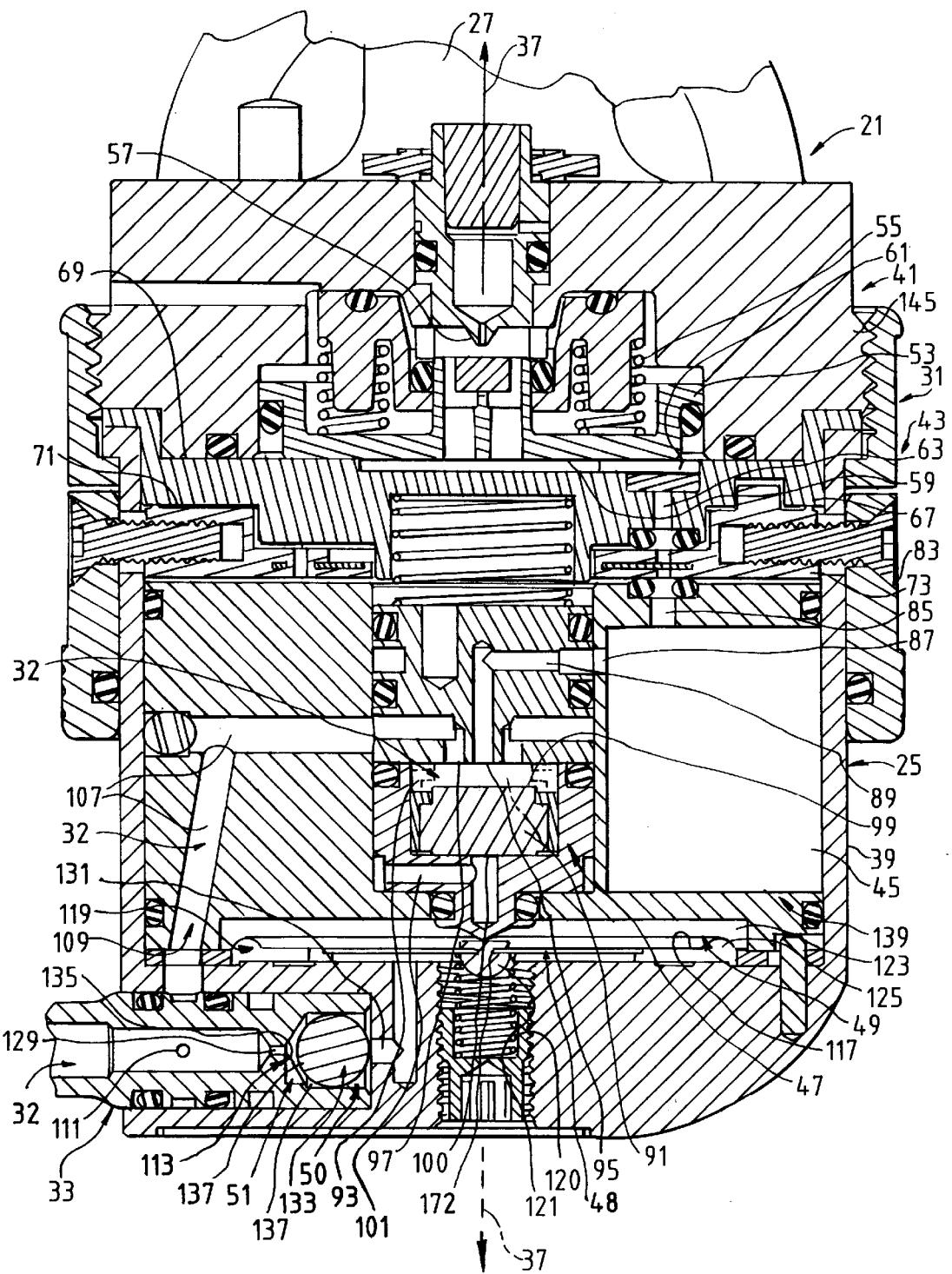
FIG. 4 is a cross-sectional view of the conserving device taken along line IV—IV of FIG. 2.

The passages, chambers, and other components within main body 31 are arranged so as to minimize distance 35 between regulator inlet 23 and delivery outlet 33, thereby rendering conserving device 21 relatively compact. As seen in FIGS. 1 and 2, main body 31 is substantially cylindrical and has a central longitudinal axis 37 about which exterior surface 39 of main body 31 is substantially symmetric.

Referring now more particularly to FIGS. 3–6, the major components or systems of conserving device 21 operate and are interconnected as follows. Regulator 41 reduces the pressure of the gas from gas source B to a delivery pressure. A flow-rate selector 43 (FIGS. 4–6) determines the rate at which the gas, at delivery pressure, flows into a rechargeable reservoir 45. Main valve 47 causes gas to be dispensed from reservoir 45 intermittently and in response to certain pressures exerted on main valve 47. Movements of a sensing valve 49 occur in part by inhalation of the person using the conserving device 21, as well as by flow of gas through a pressure line 105 in cooperation with backflow through a sensing passage 50 of device 21, as will be explained in more detail subsequently.

In general terms, then, conserving device 21 includes a delivery system 32 which has certain passages and valves in pneumatic communication with the reservoir 45, (including main valve 47, for example), with other systems, and with the person, so as to open and close reservoir outlet 87 and dispense gas intermittently from reservoir 45 to the person. Conserving device also includes certain passages and valves (including sensing valve 49, for example) which form sensing system 48, which is in pneumatic communication with the person to receive gas to detect a pressure drop upon inhalation by the person. Sensing system 48 is likewise in pneumatic communication with delivery system 32 to cause the delivery system 32 to open reservoir outlet 87 in response to detecting the pressure drop mentioned above. A gas control system 90 is pneumatically connected to the gas source, to delivery system 32, and to sensing system 48.

Certain passages of gas control system 90 (including pressure line 105 and sensing passage 50, for example) are sized and established so that gas control system 90 increases pressure in the sensing system 48 when gas control system 90 receives gas from delivery system 32 and causes reservoir outlet 87 to close and thereby interrupt the delivery of gas to the person, in response to the increased pressure in sensing system 48.

The systems 32, 48, and 90 are operatively interconnected so that an oxygen-rich pulse is delivered to the person during the first half of the person's inspiratory cycle, that is, the person's inhalation, which time period has been identified as a useful and desirable moment for the person to receive oxygen. Furthermore, delivery of the oxygen pulse is preferably performed through any standard single-lumen cannula rather than the dual-lumen cannula typically found in pneumatic oxygen conserving devices.

A sensing passage 50 is pneumatically connected to the gas delivery outlet 33 and sensing valve 49 so as to better conserve oxygen, while at the same time maintaining a desirable oxygen delivery profile and thus not deprive the person of needed oxygen. In this embodiment, sensing passage 50 includes an optional check valve 51. Check valve 51, in combination with other components of conserving device 21, operates to interrupt the flow of oxygen independently of exhalation of the patient.

By filling reservoir 45 at a rate selected by flow-rate selector 83, a corresponding "flow minute volume", that is, a volume of oxygen per minute, is delivered to the patient generally without regard to the number of breaths taken by the patient per minute. In other words, the pneumatic connections of reservoir 45 allow the conserving device 21 to be self-regulating: more rapid breathing by the person will deliver smaller but more frequent pulses of oxygen, whereas less rapid breathing will deliver larger and correspondingly less frequent pulses of oxygen, in either event, resulting in the same volume of gas delivered per minute.

Regulator 41 delivers gas from gas source B at a predetermined delivery pressure by means of a disk 53 biased by suitable means, here shown as multiple springs 55. Gas enters regulator 41 through regulator orifice 57, travels through various passages to the back side 59 of disk 53 and thereby overcomes the biasing of springs 55 to a sufficient degree to create the desired delivery pressure at the back side 59.

Operation and construction of regulator 41 is generally well-known in the art, one suitable example being disclosed in U.S. Pat. No. 5,899,223, of common assignee, the teachings of which are incorporated herein by reference.

Figure 5:
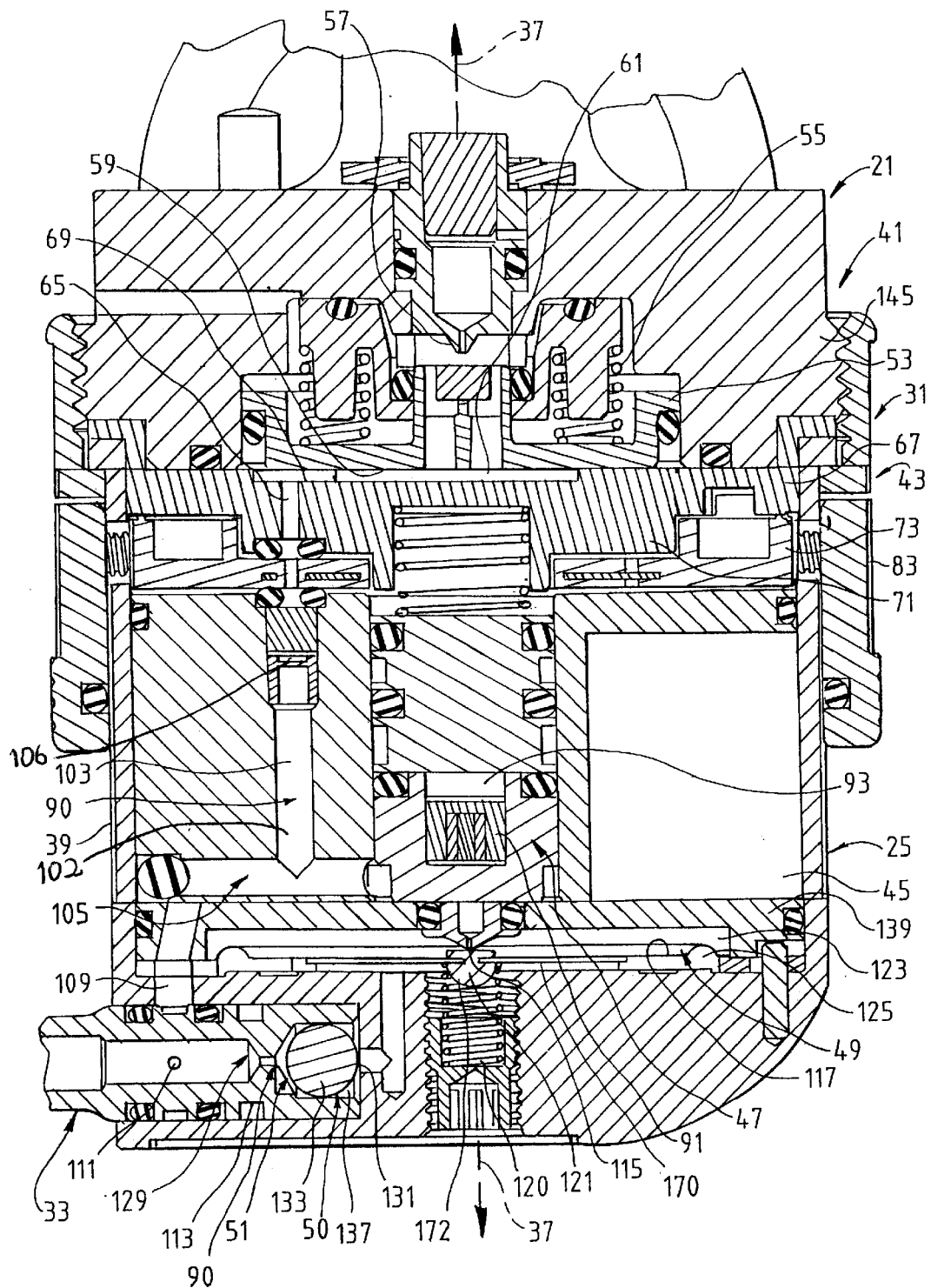
FIG. 5 is a cross sectional view taken along line V—V of FIG. 1.

Gas at a desired delivery pressure, 50 psi in this preferred embodiment, is present in region 61 adjacent to backside 59 of disk 53. From regions 61, gas flows through flow-rate selector 43 through two passages: a variable-rate passage 63 (FIG. 4) and a pressure passage 65 (FIG. 5). Passages 63, 65 extend, in part, through flow-rate selector cap 67. Cap 67 has a surface 69 which opposes regulator 41 and forms part of region 61 containing gas at the delivery pressure. Cap 67 includes a second surface 71 opposite surface 69. Surface 71 is shaped to receive orifice plate 73 in a substantially opposing relationship thereto. Orifice plate 73, shown in more detail in FIGS. 11–13 includes three sets of orifices 75, 77 and 79 extending between opposite planar surfaces of orifice plate 73. The orifices of each set 75, 77, and 79 are spaced at predetermined angles from each other. Each set of orifices is located at a corresponding radial distance from center 81 of orifice plate 73.

Orifice set 75 comprise the so-called variable rate orifices by including orifices of diameters varying between 0.00101 to 0.004 inches. Orifice set 77 comprise the so-called constant rate orifices by including orifices having the same diameter, preferably about 0.036 inches. Orifice set 79 comprises vent orifices for allowing gas to escape main body 31 at predetermined rates to improve the delivery of oxygen to the person.

Orifice plate 73 is coaxially mounted to cap 67 and is rotatable relative thereto so that the user can position a selected one of the variable rate orifices 75 into variable rate passage 63 to deliver gas through such passage at the desired rate. Similarly, the set of constant rate orifices 77 is positioned so that a selected one of such orifices is interposed within pressure passage 65 whenever gas is flowing through the variable rate passage 63.

Flow-rate selector 43 is further provided with a ring or knob 83 to enable the person to readily rotate orifice plate 73 to the desired flow-rate setting. Suitable indicia (not shown) can be provided to indicate the amount of gas flowing through the variable-rate passage. In this preferred embodiment, the volume passing through the variable Variable-rate passage 63 is pneumatically connected to reservoir inlet 85 of reservoir 45. A reservoir outlet 87 is also defined in reservoir 45, which outlet 87, in turn, leads to passage 89. Passage 89, in turn, extends to and pneumatically communicates with main valve 47.

Main valve 47 is formed by having a movable element, preferably a piston 91, which reciprocates within a chamber 93. Chamber 93 has a chamber inlet 95 at the end of passage 89, thereby in pneumatic communication with reservoir outlet 87. Chamber 93 also has a chamber outlet 97 defined therein. Chamber inlet 95 and chamber outlet 97 are preferably located to one side 99 of piston 91. On the opposite side 100 of piston 91, a pressure inlet 101 (FIG. 4) is defined in chamber 93. Pressure inlet 101 is pneumatically connected to constant rate passage 65 in cap 67 by means of intermediate passage 103, as best seen in FIG. 5.

The pressure passage 65, intermediate passage 103, and pressure inlet 101 together comprise a pressure line 105 which exerts sufficient pressure on side 100 of piston 91 to urge piston 91 upward under certain pressure conditions. When piston 91 is urged upwardly to its limit position, main valve 47 is in the closed position, that is, reservoir outlet 87 is closed, thereby permitting reservoir 45 to become filled with gas flowing through reservoir inlet 85. The upper position of piston 91, during which it closes reservoir outlet 87, is shown in phantom lines in FIG. 4.

Conversely, when piston 91 reciprocates to its lower position shown in solid lines, reservoir outlet 87 is open, permitting gas to flow from reservoir 45 for delivery to the patient. More particularly, gas for delivery to the user flows from chamber outlet 97 through delivery passage 107 (FIG. 4) which terminates at a delivery end 109 adjacent to delivery outlet 33. Gas exits delivery end 109 and enters delivery outlet 33 through a plurality of side bores 111 defined in a fitting 113. Fitting 113 is, in turn, connected to single-lumen cannula C (FIG. 1) for delivery to the user.

The foregoing has described the main components of conserving device 21 and how they deliver gas to the user. It will now be explained how the conserving device 21 interrupts gas delivery, that is, conserves gas by delivering it when called for by the person. Pressure line 105 communicates not only with chamber 93 of main valve 47 but also with sensing valve 49 through port 115. Sensing valve 49 includes a sensing chamber 119 defined within main body 31 in communication with a port 115. A sensing element 117 is disposed within sensing chamber 119. Sensing element 117 preferably comprises a diaphragm with a suitable reinforced portion 121 which opposes port 115. Sensing element 117 is biased against port 115 by means of spring 120.

Figure 6:
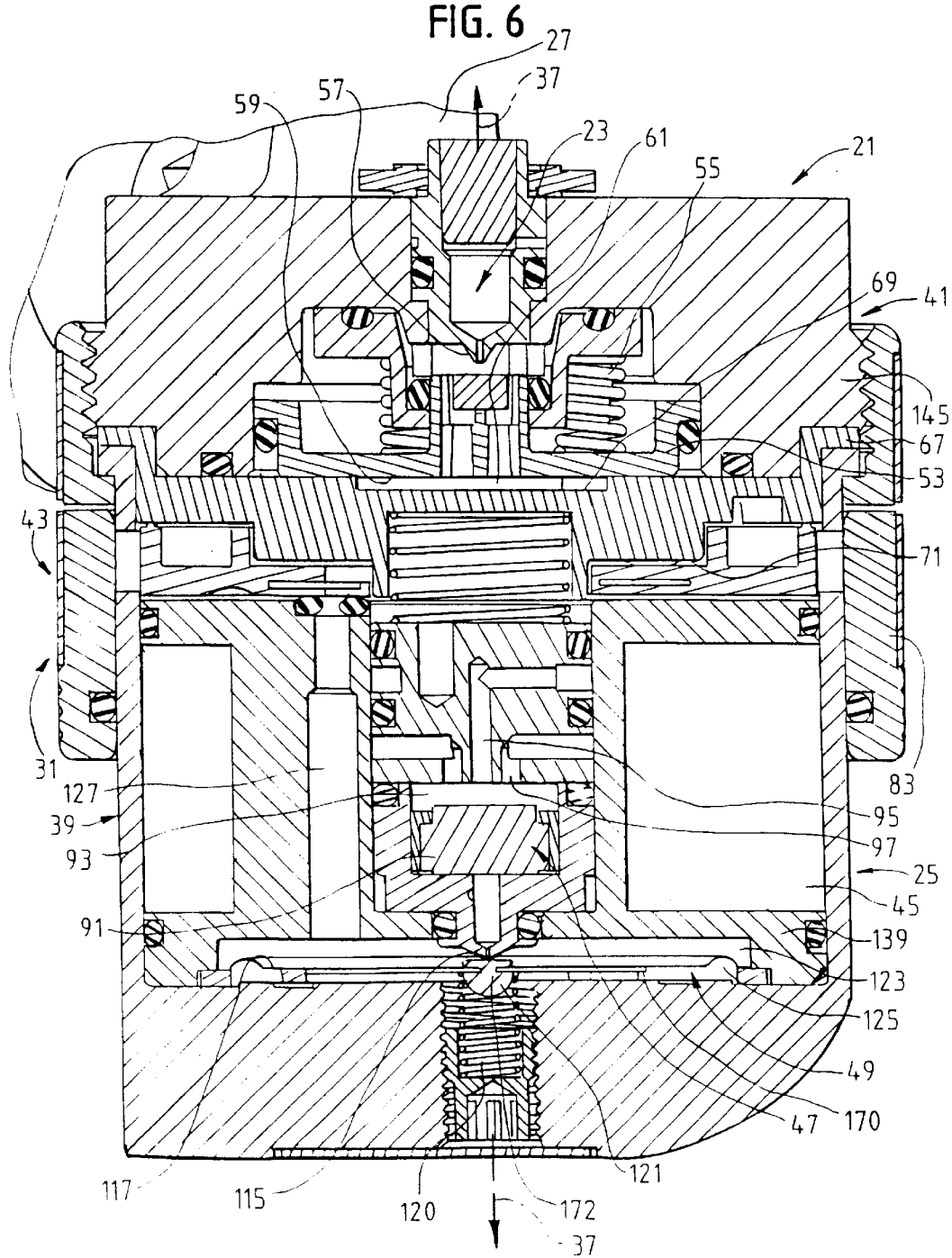
FIG. 6 is a cross sectional view taken along line VI—VI of FIG. 2.
Figure 7:
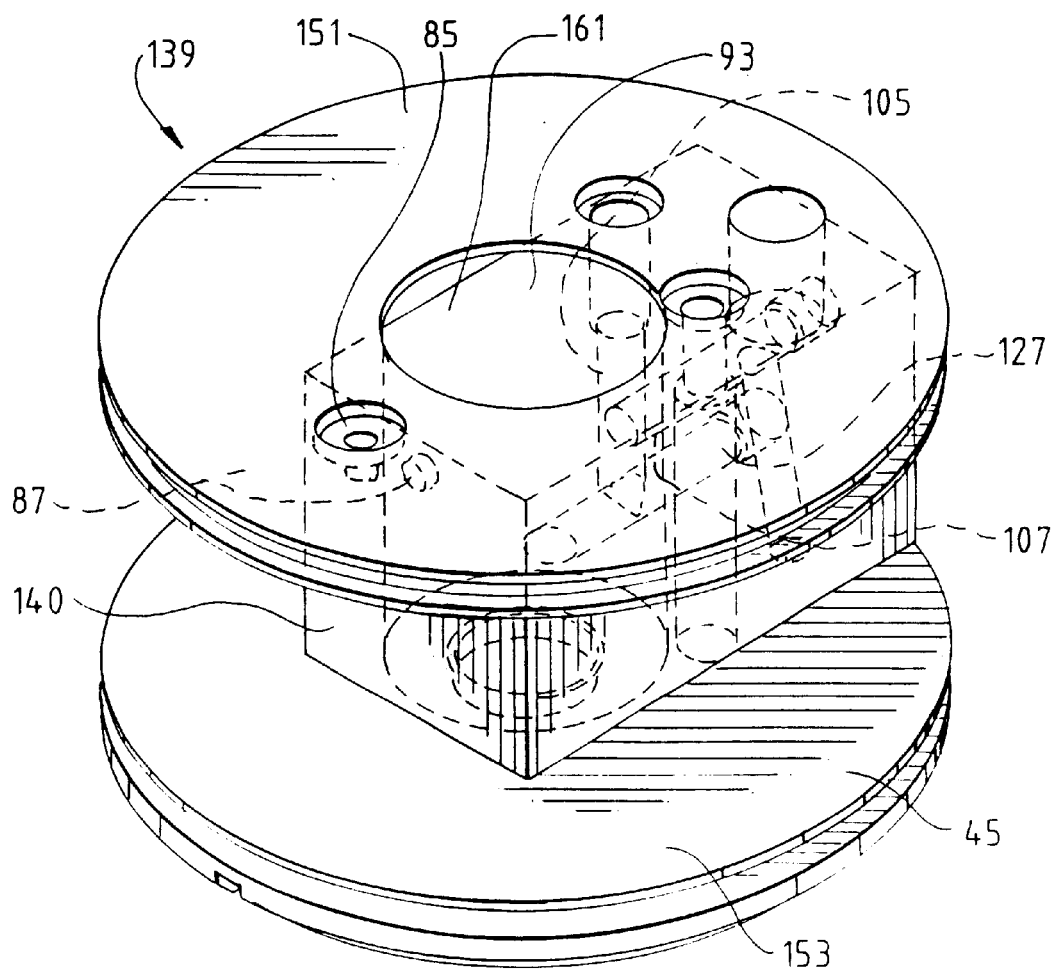
FIGS. 7 and 8 are perspective and top plan views, respectively, of one of the components of the conserving device of FIGS. 2 through 6.
Figure 8:
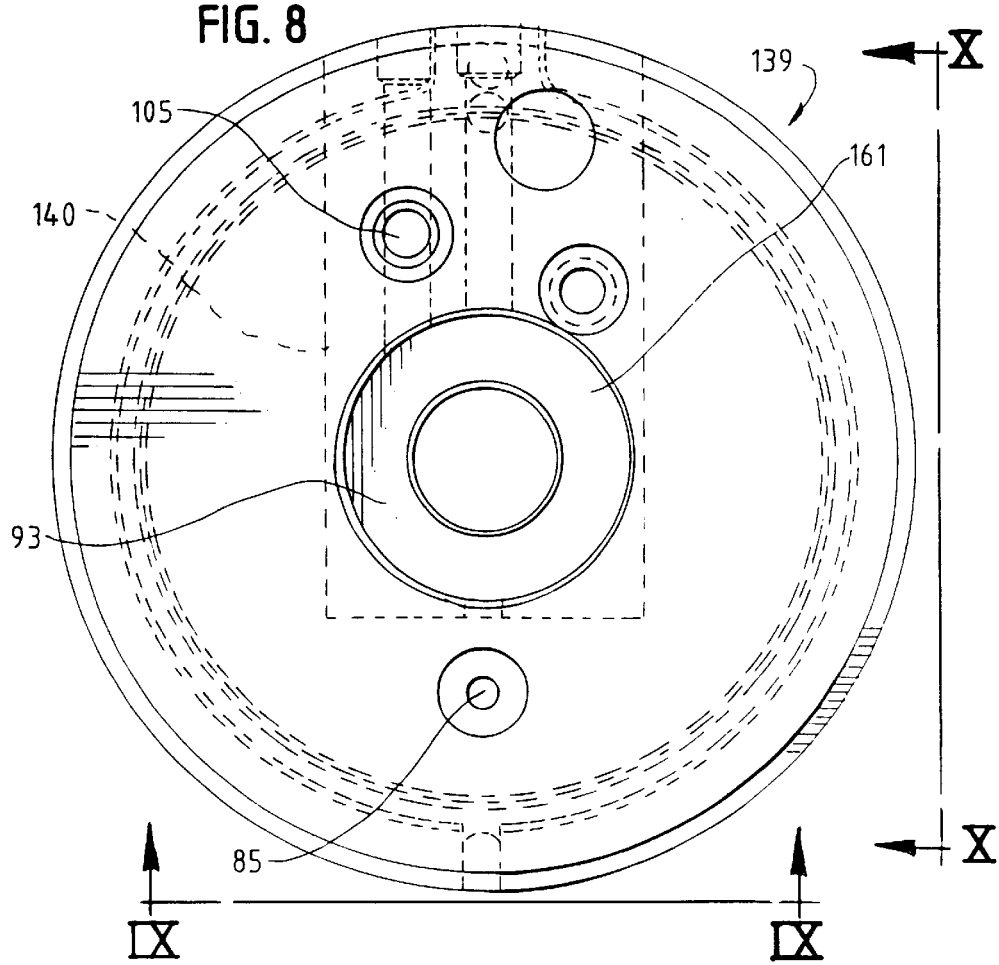
Figure 9:
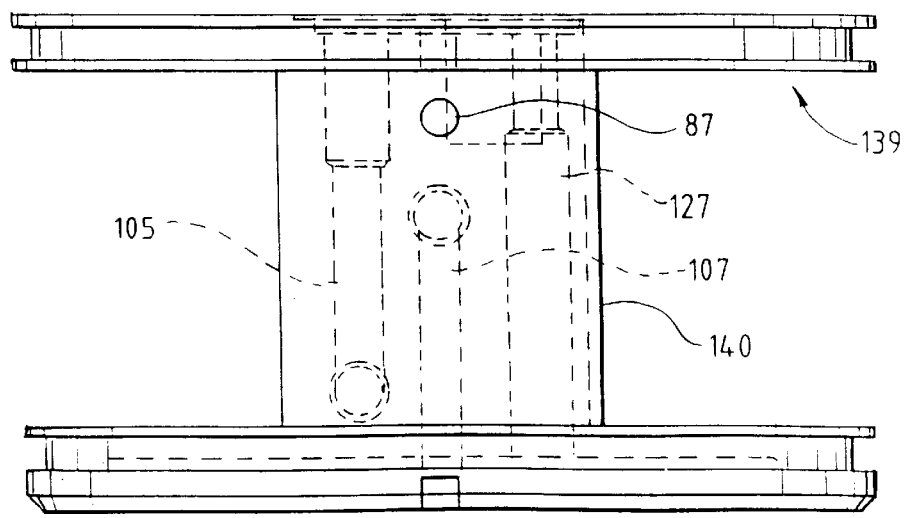
FIGS. 9 and 10 are two side views of the component of FIGS. 7 and 8.
Figure 10:
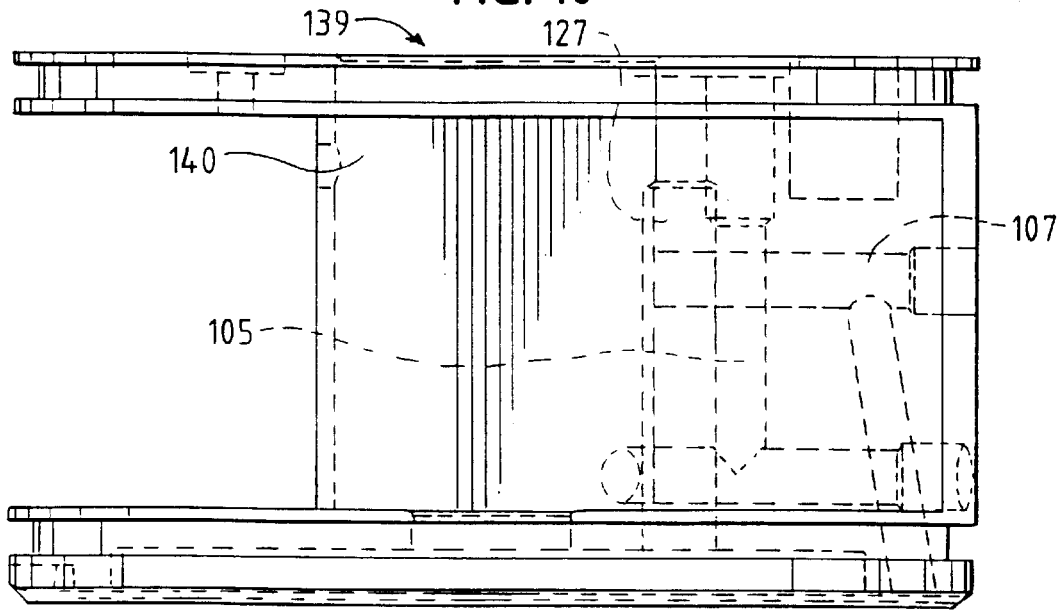

Sensing element 117 divides sensing chamber 119 into two regions: a first region 123 in pneumatic communication with port 115, and a second region 125 in pneumatic communication with delivery outlet 33. Region 123, as seen in FIG. 6, has a vent to atmosphere 127 extending from it.

When sensing valve 49 is in the closed position, sensing element 117 is positioned to seal port 115. Conversely, when sensing valve 49 is open, sensing element 117 is spaced from port 115, thereby allowing gas from pressure line 105 to flow therethrough. When gas flows from pressure line 105 through port 115, such gas is vented through the vent to atmosphere 127 at a predetermined rate.

Sensing passage 50 is disposed between and in pneumatic communication with delivery outlet 33 and sensing valve 49. Sensing passage 50 has a first opening or subpassage 129 communicating with delivery outlet 33 and a second opening or subpassage 131 communicating with region 125 of sensing valve 49. First opening 129 is sized so that the pressure of gas being dispensed through delivery outlet 33 is not immediately or fully transmitted to sensing valve 49. Otherwise stated, the cross-sectional area of opening 129 is relatively smaller than the cross-sectional areas adjacent such opening 129, creating a corresponding restriction at a medial location in sensing passage 50. Check valve 51 increases assurances that appropriate pressures are transmitted from gas under delivery to sensing valve 49. Check valve 51 includes a check element 133 received in a chamber 137 of check valve 51. Check element 133 is movable between the two openings 129, 131 in response to pressure differences between opposing sides of check element 133. When check element 133 abuts second opening 131, opening 131 is substantially sealed. However, when check element 133 abuts first opening 129, a complete seal is not formed because a counterbore 135 extends from opening 131 into chamber 137. Check element 133 and counterbore 135 are suitably formed so that counterbore 135 is not sealed by the outer surface of check element 133 even when check element 133 is brought against first opening 129.

Delivery passage 107 terminates in delivery outlet 33 at a location so that passage 107 communicates with first opening 129 of check valve 51. Otherwise stated, gas exits delivery passage 107 on the "delivery side" of check valve 51.

In operation, when the user inhales through cannula C, a lower than ambient condition or vacuum is transmitted through cannula C to the delivery outlet 33. The resulting vacuum passes through sensing passage 50 and acts to open sensing valve 49. In this embodiment, check element 133 moves toward opening 129 a sufficient amount to unseat it from opening 131. By virtue of counterbore 135, sensing passage 50 comprises a continuous air passage between region 125 of sensing valve 49, that is, "on the delivery side" of sensing element 117, such air passage extending through check valve 51 and into cannula C. The vacuum created by inhalation thus draws air from region 125 of sensing valve 49. The flow of air in this manner is sufficient to overcome the bias of spring 120 and separate sensing element 117 from port 115.

Once port 115 is open, gas from the pressure line 105 flows out port 115 and escapes the main body 31 of the device 21 through vent to atmosphere 127. Although gas exiting port 115 is being vented to atmosphere, a certain amount of back pressure is maintained in region 123 of sensing chamber 119 by virtue of venting orifices 79 which slow the flow of gas out of the vent to atmosphere 127. Vent orifices 79 have sizes selected to maximize the oxygen delivery profile corresponding to respective volumes of the variable-rate orifice set 75. Otherwise stated, the back pressure created by the venting orifices 79 generally keeps port 115 open for a slightly longer period which, in turn, continues delivery of oxygen for a correspondingly longer period as well.

When a sufficient amount of gas from the pressure line 105 escapes through vent to atmosphere 127, the pressure which previously kept the piston 91 in sealing engagement with reservoir outlet 87 is sufficiently reduced so that piston 91 reciprocates away from reservoir outlet 87 to open outlet 87. Once reservoir outlet 87 is open, gas stored in reservoir 45 under a predetermined pressure escapes through outlet 87 into chamber 93 of main valve 47 and then exits chamber 93 through chamber outlet 97 to enter delivery passage 107. From delivery passage 107, gas exits delivery outlet 33 and flows to the person through cannula C.

Significantly, as gas exits delivery passage 107 through delivery end 109, the pressure of the gas during delivery is felt in sensing passage 50. As a result, check element 133 moves against and seals opening 131. The seating of check element 133 in this fashion returns region 125 of sensing valve 49 to a higher pressure, preferably approaching atmospheric, such pressure being sufficient to allow spring 120 to reseat sensing element 117 against port 115. Once port 115 has been resealed by sensing element 117, pressure line 105 repressurizes region 123 of sensing valve 149 and, importantly, the region adjacent to the lower side of piston 91. Bottom side 100 of piston 91 has a sufficiently large surface area so that once gas pressure reaches a certain level in the region adjacent to surface 100, piston 91 reseats in the upper, closed position to reseal reservoir outlet 87.

The sealing of reservoir outlet 87 interrupts the flow of oxygen being delivered to the patient. In this way, pulses of oxygen are delivered to the person, such pulses substantially corresponding to the release of gas stored in reservoir 45. In addition, the size and length of the oxygen pulse is regulated in substantial part by the outflow of the pulse from the device, rather than by exhalation of the person, with the result that the oxygen pulse better matches the demand for oxygen under most circumstances. As such, conservation of oxygen is accomplished while also fulfilling the recommended oxygen delivery profiles of persons using the device.

One such oxygen delivery profile has been graphed in FIG. 14. In general terms, the solid line charts the person's or the patient's inspiratory cycle, that is, the inhalation and exhalation of the patient. The onset of inhalation or inspiration is shown as a slight spike occurring approximately at 0.4 seconds and again at 3.4 seconds, and measured as an increase in pressure in cannula C. It has been found desirable to deliver as much oxygen, that is, as much of the pulse as possible, within the first half second of inspiration. The device 21, according to the present invention, generally accomplishes such goal, as shown by the graph of FIG. 14. In particular, the dotted line charts the delivery of the oxygen pulse, which starts at approximately 0.6 seconds (approximately 0.2 seconds after inspiration) and lasts for about 0.3 seconds or less, meaning that most of the oxygen has been delivered within the first half second after the patient inspiration.

The task of delivering most oxygen within the first half second of inspiration becomes progressively more difficult as larger volume pulses need to be delivered. The components of device 21 described above include features which enhance the oxygen delivery profile and generally allow for rapid delivery even of high volume oxygen pulses at the outset of inspiration, generally within about the first one-half second. This is generally accomplished by providing for main valve 47 to reciprocate or open and close very rapidly, in a so-called "snap action", which action permits a rapid, high-volume spike of oxygen to be quickly delivered at the onset of inspiration.

Such rapid reciprocation of main valve 47 involves reciprocation of moveable element 91 within chamber 93 of main valve 47. When main valve 47 is closed, moveable element 91 is in its upper position, as oriented in the drawings, in which its upper side 99 seals chamber inlet 95 and chamber outlet 97 and thereby closes off reservoir 45 from delivery. When sealed in this manner, pressure line 105 exerts pressure across substantially the whole area of lower or opposite side 100 of moveable element 91, whereas upper side 99 is only acted upon by pressure across a relatively smaller area corresponding to the area of chamber inlet 95. The difference in pressure exerted over surface areas on opposite side 99, 100 of moveable element 91 maintains moveable element 91 sealed in its upper position.

Upon inhalation, however, the force exerted on bottom side 100 of piston 91 begins to reduce, as pressure line 105 is gradually relieved, that is, vented to atmosphere in this embodiment. When the pressure exerted on side 100 of moveable element 91 drops sufficiently, the pressure on opposite, upper side 99 is sufficient to slightly unseal chamber inlet 95, that is, the previous seal of reservoir 45 is "cracked open". As soon as upper side 99 slightly unseals from chamber inlet 95, substantially all of the surface area of the side 99 becomes exposed to pressure of gas storage in reservoir 45, rather than the more reduced area of inlet 95 previously exposed to such pressure when upper side 99 was sealed thereagainst. The sudden increase of surface area rapidly increases the downward force (as oriented by the drawing) exerted on moveable element 91, which, in turn, causes element 91 to reciprocate or "snap" downward rapidly.

In such downward or lower position, bottom side 100 of moveable element 91 seals pressure line 105. By virtue of the fact that pressure line 105 has a pressure inlet 101 with a smaller surface area than upper surface 99, when inlet 101 is sealed, a relatively smaller force is exerted against bottom side 100 than against opposite side 99, which pressure imbalance keeps pressure line 105 sealed during most of the oxygen delivery.

Once the pressure from reservoir 45 has been sufficiently reduced by delivery of oxygen therefrom, the force exerted against upper side 99 is reduced so that the opposing force exerted on lower side 100 slightly unseals lower side 100 from pressure inlet 101. Again, as explained previously, this slight unsealing immediately expands the surface area of lower side 100 over which pressure from pressure line 105 acts. Such expansion of surface area, in turn, rapidly increases the upward force (as oriented in relation to the drawings), which, in turn, reciprocates moveable element 91 rapidly and upwardly in a "snap action", after which it again seals in the upper position to close off oxygen delivery from reservoir 45.

The rapid reciprocation of main valve 47 delivers the steep, oxygen-rich pulses shown in the graph of FIG. 14 at the beginning moments of inspiration, when most desirable.

In the preferred embodiment, by about the end of the first tenth of a second, device 21 senses inspiration by the patient, such "sensing" corresponding to the small bump in the dotted line, which indicates sensing valve 49 has opened. By about the lapse of the second tenth of a second, air under the main valve (adjacent to lower side 100) escapes through port 115 to relieve pressure line 105 and main valve 47 unseals slightly from chamber inlet 95, which then causes main valve 47 to "snap open." Between about the second tenth of a second and the third tenth of a second, the delivery of a pulse of oxygen from reservoir 45 commences and lasts for about three tenths of a second. At about 0.45 seconds, sense diaphragm 119 closes and begins pressurizing under main valve 47. After about five tenths of a second, the pressure differential has been reduced sufficiently in main valve 47 so that moveable element 91 slightly unseals from pressure inlet 101, after which it "snaps" or reciprocates rapidly upwardly to close reservoir 45.

Because gas continually flows into reservoir 45 through variable-rate passage 63 of the flow-rate selector 43, when reservoir outlet 87 is sealed by piston 91, reservoir 45 becomes pressurized with gas entering through reservoir inlet 85.

When the person once again inhales, the volume of pressurized gas stored in reservoir 45 is released and main valve 47 is opened, whereupon the delivery cycle described above is repeated. The foregoing cycle repeats indefinitely so long as gas remains in gas source B.

Pressure line 105 is preferably equipped with a constriction 106 (FIG. 5) selected to reduce the rate of repressurization at the bottom of piston 91. By slowing the rate of repressurization, reservoir outlet 87 remains open for an amount of time sufficient to deliver the desired oxygen pulse before closing.

The profile of the oxygen pulses is also affected by the set of venting orifices 79. Such orifices 79 are positioned so that a selected on of the orifices is interposed in the vent to atmosphere 127. The selected orifice slows the escape of gas through vent to atmosphere 127, thereby creating a certain amount of back pressure in region 123 of sensing valve 49. This back pressure, in turn, keeps sensing element 117 from reseating against port 115. By keeping sensing valve open for longer, the region below piston 91 is not repressurized as quickly which, in turn keeps main valve 47 open to deliver oxygen for longer.

The need to deliver oxygen for longer periods is more prevalent when higher volume minute rates of oxygen delivery are needed. Accordingly, smaller vent orifices 79 are interposed in vent to atmosphere 127 when correspondingly larger variable rate orifices 75 are interposed in variable rate passage 63. The different sized orifices which can be selectively interposed in variable rate passage 63 are referred to as different "settings" on the device, which would be associated with indications (not shown) on the knob 83. In this preferred embodiment, the variable rate orifices 75 and vent orifices 79 correspond as follows, expressed in inches: setting 1 has a 0.004 variable rate orifice 75 and a 0.012 vent orifice 79, setting 2 has a 0.0062 variable rate orifice 79 and a 0.013 vent orifice, setting 3 has a 0.0077 variable rate orifice 79 and a 0.015 vent orifice, setting 4 has a 0.0092 variable rate orifice 79 and a 0.017 vent orifice, and setting 5 has a 0.00101 variable rate orifice 79 with a 0.08 vent orifice.

There is sometimes a need to deliver oxygen in a constant, uninterrupted manner. Device 21 accomplishes such "continuous flow" deliver by a suitable positioning of the orifice plate, in which variable rate orifice 79 is 0.0092.

Figure 11:
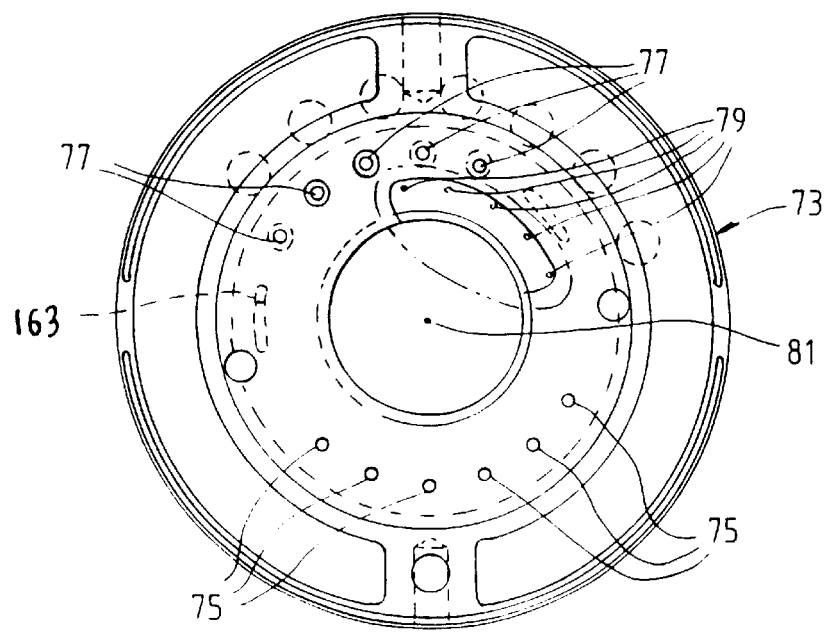
FIGS. 11, 12, and 13 are top, bottom, and side sectional views, respectively, of another component of the oxygen conserver of the present invention.
Figure 12:
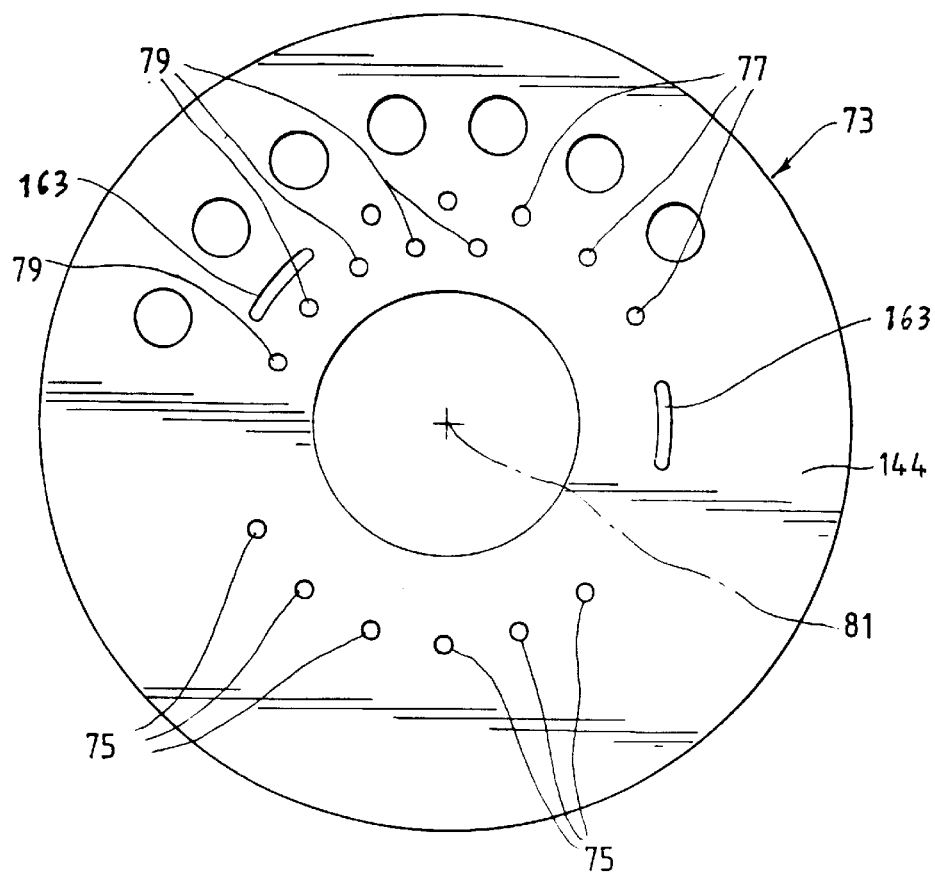
Figure 13:
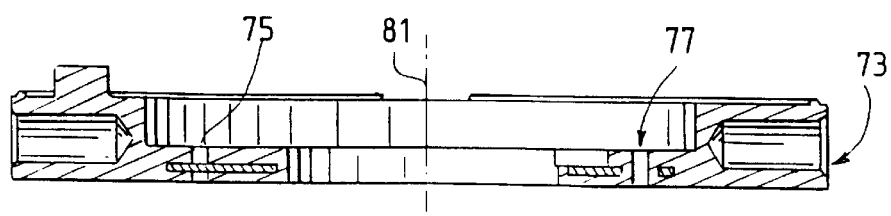

Referring to FIGS. 11 and 12, orifice plate 73 has been equipped with elongated cavities or grooves 163, which are located at the same radial distance from center 81 as constant rate orifices 77. Cavities 163 do not extend transversely through the entire width of orifice plate 73, but rather are formed to extend only partly through plate 73 from planar service 144 (FIG. 12) thereof. Planar surface 144, in turn, opposes disk 151 of plate 139. Accordingly, when orifice plate 73 is rotated so that grooves 163 are aligned with pressure passage 65, pressure passage 65 is blocked, whereas grooves 163 permit pressure line 105 to communicate with the ambient. (FIG. 5). By maintaining pressure line 105 in communication with the ambient, it is assured that flow through device 21 will remain continuous, since main valve 47 remains open.

There are two grooves 163, one of which provides for constant flow as outlined above. The second groove 163 serves as a "failsafe" to avoid undesirable pressure buildup within device 21 in the event of a malfunction when the flow is turned off through such device Main body 31 of conserving device 21 has the various device components arranged therein to reduce the length, size and bulk of device 21. For example, a plate 139, best seen in FIGS. 7–10, includes upper and lower discs 151, 153 held in longitudinal, spaced relationship from each other by an intermediate element 140. Element 140 is generally box shaped, with one vertical wall proximate to the circumference of the discs 151, 153 along a portion of the arcs of such circumferences. Chamber 93 of main valve 47 is defined in one portion of element 140, whereas delivery line 107, pressure line 105, and vent to atmosphere 127 are substantially defined in another portion of element 140 to one side of chamber 93. This side-by-side arrangement of chamber 93 and its various related passages avoids increasing the overall length of conserving device 21.

Similarly, reservoir 45 is defined between the two discs 151, 153 and extends in a "C" shape surrounding element 140. Discs 151, 153 are sealed against the inner wall of housing 25 to create the appropriate air-tight conditions in reservoir 45. Again, the location of reservoir 45 in a surrounding relationship to element 140 avoids increasing the overall length of conserving device 21.

Disc 151 opposes orifice plate 73. Accordingly, disc 151 has reservoir inlet 85 defined therein at a location to correspond to variable rate passage 63 (FIG. 4) to receive oxygen into the reservoir at a selected minute volume. Disc 153, in turn, opposes sensing valve 49 and also faces delivery outlet 33. Accordingly, delivery passage 107 has a terminal portion exiting through disc 153.

Regulator 41, flow-rate selector 43, and plate 139 are secured to each other along longitudinal axis 37. In this preferred embodiment, regulator 41, flow-rate selector 43, and plate 139 are each substantially cylindrical and have central axes mounted coaxially with longitudinal axis 37 of main body 31. As best seen in FIG. 3, main body 31 includes an end cap 143, the outer surface of which forms a substantial part of external housing 25 of device 21. End cap 43 is secured to a corresponding base member 145 by a collar 147.

Suitable openings and seals 148 are interposed between subcomponents of device 21 in a manner known in the art to foster the necessary pneumatic communications as well as to isolate passages and chambers from each other as required. The counterbore 135 preferably has an effective diameter of 15–18 thousandths of an inch, and the constriction in the pressure line 105 is preferably about 2 thousandths of an inch.

Piston 91 of main valve 47 is preferably and primarily formed of polymeric material and is received in a piston insert 149. Piston insert 149, in turn, is received in a friction fit in bore 161 in plate 139, which bore 161 corresponds to chamber 93 of main valve 47.

The port 115 of sensing valve 49 preferably has a size of 0.008 inches. Sensing element 117 preferably comprises a diaphragm with the following characteristics: a 1.43" diameter ring 166 (FIG. 3) is formed at the outer edge thereof. The ring 166 is 0.050" thick at this point and acts as a seal and a foundation. Connected to this ring is a convolute 168 that acts as a hinge. A center plate 170 extends inwardly from convolute 168. A seat 172 (FIGS. 4–6) is secured to center plate 170 and located to open or close port 115. One side of seat 172 opposes port 115, while the other side of seat 172 is formed into a spring boss 174 which receives spring 120 thereon. The diaphragm is secured within sensing chamber 119 by the ring 166, the convolute allows the center plate to move in and out, and the seat opens and closes the 0.008 orifice. Inspiration overcomes the force of spring 120 to open the seat 172.

The check element of check valve 51 preferably comprises a nylon check ball with a diameter of 0.187 inches received in chamber 137 of diameter of 0.196 inches.

Plate 139, orifice plate 73, base 145, end cap 143, flow-rate selector 43, and regulator 41, are generally made of machined metal, preferably aluminum. Non-metallic plugs, seals and the like are provided in a manner generally known to the art to interconnect or isolate the components of device 21.

In addition to the advantages apparent from the forgoing description, conserving device 21 delivers a pulse of gas on demand, in accordance with generally accepted gas delivery profiles, and interrupts the flow of gas when no longer needed, thus lengthening the useful life of a finite source of pressurized gas.

As a further advantage, the device according to the present invention can be used with a variety of common single-lumen cannulas.

As a still further advantage, the components of the invented device render the overall device lightweight, portable, and compact.

Yet another advantage to the invention resides in its self-regulating nature, that is, delivering more voluminous pulses of oxygen in the event of slower breathing and less voluminous pulses in the event of more rapid breathing, all while maintaining substantially the same minute volume of gas delivery.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. A conserving device for use in delivering gas from a source of gas through a gas line to a patient, the conserving device comprising:

a reservoir having an inlet for receiving the gas into the reservoir and an outlet for discharging the gas from the reservoir;

a main valve in pneumatic communication with the outlet of the reservoir and operable between a closed position for closing the outlet to pressurize the reservoir and an open position for opening the outlet to depressurize the reservoir;

a pressure line extending pneumatically and communicating between the source of the gas and the main valve to bias the main valve towards the closed position, the pressure line terminating in a port;

a sensing valve in pneumatic communication with the port and operable between a closed position to close the port and an open position to open the port and allow the gas from the pressure line to flow therethrough;

a delivery outlet in pneumatic communication with the outlet of the reservoir and the gas line to deliver the gas discharged from the reservoir;

a sensing passage communicating between the delivery outlet and the sensing valve;

wherein, in response to inhalation by the patient through the gas line connected to the delivery outlet, air is drawn through the sensing passage and from the sensing valve to move the sensing valve to the open position to open the port, whereupon the biasing of the main valve is sufficiently reduced for the main valve to move to the open position, whereupon the outlet to the reservoir is opened and the gas therein is discharged from and exits through the delivery outlet to the patient; and wherein the sensing passage is disposed relative to the delivery outlet so that a portion of the gas flowing into the delivery outlet passes through the sensing passage to bias the sensing valve toward the closed position, the sensing valve closing the port when predetermined pressures are achieved in the sensing valve, whereupon the gas from the pressure line moves the main valve to close the reservoir outlet, interrupting delivery of the gas to the patient and permitting repressurizing of the reservoir, whereby the gas is delivered intermittently and is conserved.

2. The device of claim 1, further comprising a vent in pneumatic communication with the port to allow gas flowing from the port to escape to the ambient.

3. The device of claim 1 further comprising a plurality of orifices disposed in spaced relation on an orifice plate, a selected one of the orifices positioned between and in pneumatic communication with the source of the gas and the inlet of the reservoir, the selected orifice corresponding to the flow of gas.

4. The device of claim 3 further comprising a pressure regulator, the pressure regulator including
a regulator inlet adapted to attach to the source of gas;
means for reducing the pressure of the source of gas to a delivery pressure, and
a regulator outlet for delivering the gas at the delivery pressure, the regulator outlet in pneumatic communication with the selected orifice of the orifice plate.

5. The device of claim 1, wherein the main valve comprises a chamber and an element received in the chamber and movable therein to cause the main valve to close and open when predetermined pressures exist within the chamber.

6. A conserving device for use in delivering gas from a source of gas through a gas line to a patient, the conserving device comprising:
a reservoir having an inlet for receiving the gas into the reservoir and an outlet for discharging the gas from the reservoir;
a main valve in pneumatic communication with the outlet of the reservoir and operable between a closed position for closing the outlet to pressurize the reservoir and an open position for opening the outlet to depressurize the reservoir;
a pressure line extending pneumatically and communicating between the source of the gas and the main valve to bias the main valve towards the closed position, the pressure line terminating in a port;
a sensing valve in pneumatic communication with the port and operable between a closed position to close the port and an open position to open the port and allow the gas from the pressure line to flow therethrough;
a delivery outlet in pneumatic communication with the outlet of the reservoir and the gas line to deliver the gas discharged from the reservoir;
a sensing passage communicating between the delivery outlet and the sensing valve; and
a vent in pneumatic communication with the port to allow gas flowing from the port to escape to the ambient;
wherein the vent comprises one of a plurality of selectable orifices corresponding to a range of rates of intermittent flow of the gas;
wherein, in response to inhalation by the patient through the gas line connected to the delivery outlet, air is drawn through the sensing passage and from the sensing valve to move the sensing valve to the open position to open the port, whereupon the biasing of the main valve is sufficiently reduced for the main valve to move to the open position, whereupon the outlet to the reservoir is opened and the gas therein is discharged from and exits through the delivery outlet to the patient; and
wherein the sensing passage is disposed relative to the delivery outlet so that a portion of the gas flowing into the delivery outlet passes through the sensing passage to bias the sensing valve toward the closed position, the sensing valve closing the port when predetermined pressures are achieved in the sensing valve, whereupon the gas from the pressure line moves the main valve to close the reservoir outlet, interrupting delivery of the gas to the patient and permitting repressurizing of the reservoir, whereby the gas is delivered intermittently and is conserved.

7. A conserving device for use in delivering gas from a source of gas through a gas line to a patient, the conserving device comprising:
a reservoir having an inlet for receiving the gas into the reservoir and an outlet for discharging the gas from the reservoir;
a main valve in pneumatic communication with the outlet of the reservoir and operable between a closed position for closing the outlet to pressurize the reservoir and an open position for opening the outlet to depressurize the reservoir;
a pressure line extending pneumatically and communicating between the source of the gas and the main valve to bias the main valve towards the closed position, the pressure line terminating in a port;
a sensing valve in pneumatic communication with the port and operable between a closed position to close the port and an open position to open the port and allow the gas from the pressure line to flow therethrough;
a delivery outlet in pneumatic communication with the outlet of the reservoir and the gas line to deliver the gas discharged from the reservoir;
a sensing passage communicating between the delivery outlet and the sensing valve;
wherein, in response to inhalation by the patient through the gas line connected to the delivery outlet, air is drawn through the sensing passage and from the sensing valve to move the sensing valve to the open position to open the port, whereupon the biasing of the main valve is sufficiently reduced for the main valve to move to the open position, whereupon the outlet to the reservoir is opened and the gas therein is discharged from and exits through the delivery outlet to the patient; and
wherein the sensing passage is disposed relative to the delivery outlet so that a portion of the gas flowing into the delivery outlet passes through the sensing passage to bias the sensing valve toward the closed position, the sensing valve closing the port when predetermined pressures are achieved in the sensing valve, whereupon the gas from the pressure line moves the main valve to close the reservoir outlet, interrupting delivery of the gas to the patient and permitting repressurizing of the reservoir, whereby the gas is delivered intermittently and is conserved;

wherein the sensing passage includes an opening at a medial location therein, the opening having a smaller cross-sectional area than adjacent areas of the sensing passage to restrict the flow of gas through the opening.

8. A conserving device for use in delivering gas from a source of gas through a gas line to a patient, the conserving device comprising:

a reservoir having an inlet for receiving the gas into the reservoir and an outlet for discharging the gas from the reservoir;

a main valve in pneumatic communication with the outlet of the reservoir and operable between a closed position for closing the outlet to pressurize the reservoir and an open position for opening the outlet to depressurize the reservoir;

a pressure line extending pneumatically and communicating between the source of the gas and the main valve to bias the main valve towards the closed position, the pressure line terminating in a port;

a sensing valve in pneumatic communication with the port and operable between a closed position to close the port and an open position to open the port and allow the gas from the pressure line to flow therethrough;

a delivery outlet in pneumatic communication with the outlet of the reservoir and the gas line to deliver the gas discharged from the reservoir;

a sensing passage communicating between the delivery outlet and the sensing valve;

wherein, in response to inhalation by the patient through the gas line connected to the delivery outlet, air is drawn through the sensing passage and from the sensing valve to move the sensing valve to the open position to open the port, whereupon the biasing of the main valve is sufficiently reduced for the main valve to move to the open position, whereupon the outlet to the reservoir is opened and the gas therein is discharged from and exits through the delivery outlet to the patient;

wherein the sensing passage is disposed relative to the delivery outlet so that a portion of the gas flowing into the delivery outlet passes through the sensing passage to bias the sensing valve toward the closed position, the sensing valve closing the port when predetermined pressures are achieved in the sensing valve, whereupon the gas from the pressure line moves the main valve to close the reservoir outlet, interrupting delivery of the gas to the patient and permitting repressurizing of the reservoir, whereby the gas is delivered intermittently and is conserved; and wherein the sensing passage comprises a check valve, the check valve having a check element with opposing sides, the first side facing the sensing valve, the second side facing the delivery outlet, the element movable in response to pressure differences between the opposing sides to open and close the check valve, the check valve having a counterbore defined therein, the counterbore being located so that the air drawn from the sensing valve during inhalation is carried from the first side to the second side of the checking element.

9. The device of claim 7, wherein the sensing valve includes opposing delivery and venting sides, and wherein, when the gas flows from the reservoir to the delivery outlet, a portion of said gas passes through the check valve, flowing from the second side of the check element to the first side, to increase the pressure on the delivery side of the sensing valve to bias the sensing valve toward the closed position.

10. A pneumatic apparatus for delivering pulses of gas from a gas delivery source through a single-lumen cannula in response to inhalation by a patient, the apparatus comprising:

a main body having an inlet for receiving gas from a gas source, an outlet delivering the pulses of gas, and a plurality of chambers defined between the inlet and the outlet;

the main body including a regulator pneumatically connected to the inlet for producing a delivery pressure for the gas exiting therefrom;

a flow-rate selector secured relative to the regulator so as to receive the gas exiting therefrom, the flow-rate selector having a pressure passage and a variable rate passage extending therethrough, the selector including a plurality of orifices defined therein, the orifices sized to correspond to selected oxygen delivery rates of the apparatus, the selector being movably mounted to position a selected one of the orifices in the variable rate passage to cause the gas to exit from the variable rate passage at a selected oxygen delivery rate;

a reservoir defined within the main body and having a reservoir inlet and a reservoir outlet, the reservoir located within the main body to receive the gas from the variable rate passage;

a main valve located within the main body, the main body comprising a chamber and a movable element received within the chamber, the chamber having a chamber inlet therein, a chamber outlet, and a pressure inlet, the chamber inlet in pneumatic communication with the reservoir outlet, and the pressure inlet in pneumatic communication with the pressure passage of the flow rate selector, the chamber inlet and the pressure inlet disposed in the chamber on opposite sides of the movable element, the movable element being movable to open and close the reservoir outlet;

a sensing valve comprising a sensing chamber with a sensing element received therein and a port defined in the sensing chamber, the sensing element movably mounted to seal the port in response to predetermined pressures in the sensing chamber, the sensing element dividing the sensing chamber into two regions;

a vent to atmosphere defined in the main body and extending between the sensing chamber and the exterior surface of the main body, the vent to atmosphere being in pneumatic communication with the first of the regions of the sensing chambers;

a delivery outlet adapted to connect to the single-lumen cannula;

a delivery passage having a delivery end communicating with the delivery outlet and a chamber end communicating with the chamber outlet, the delivery passage receiving gas from the chamber received from the reservoir;

a sensing passage disposed within the main body, the sensing passage having a first opening communicating with the delivery outlet and the delivery passage, and a second opening communicating with the second of the regions of the sensing chamber.

11. A pneumatic apparatus for delivering pulses of gas from a gas delivery source through a single-lumen cannula in response to inhalation by a patient, the apparatus comprising:

a main body having an inlet for receiving gas from a gas source, an outlet for delivering the pulses of gas, and a plurality of chambers defined between the inlet and the outlet;

the main body including a regulator pneumatically connected to the inlet for producing a delivery pressure for the gas exiting therefrom;

a flow-rate selector secured relative to the regulator so as to receive the gas exiting therefrom, the flow-rate selector having a pressure passage and a variable rate passage extending therethrough, the selector including a plurality of orifices defined therein, the orifices sized to correspond to selected oxygen delivery rates of the apparatus, the selector being movably mounted to position a selected one of the orifices in the variable rate passage to cause the gas to exit from the variable rate passage at a selected oxygen delivery rate;

a reservoir defined within the main body and having a reservoir inlet and a reservoir outlet, the reservoir located within the main body to receive the gas from the variable rate passage;

a main valve located within the main body, the main body comprising a chamber and a movable element received within the chamber, the chamber having a chamber inlet therein, a chamber outlet, and a pressure inlet, the chamber inlet in pneumatic communication with the reservoir outlet, and the pressure inlet in pneumatic communication with the pressure passage of the flow rate selector, the chamber inlet and the pressure inlet disposed in the chamber on opposite sides of the movable element, the movable element being movable to open and close the reservoir outlet;

a sensing valve comprising a sensing chamber with a sensing element received therein and a port defined in the sensing chamber, the sensing element movably mounted to seal the port in response to predetermined pressures in the sensing chamber, the sensing element dividing the sensing chamber into two regions;

a vent to atmosphere defined in the main body and extending between the sensing chamber and the exterior surface of the main body, the vent to atmosphere being in pneumatic communication with the first of the regions of the sensing chambers;

a delivery outlet adapted to connect to the single-lumen cannula;

a delivery passage having a delivery end communicating with the delivery outlet and a chamber end communicating with the chamber outlet, the delivery passage receiving gas from the chamber received from the reservoir;

a sensing passage disposed within the main body, the sensing passage having a first opening communicating with the delivery outlet and the delivery passage, and a second opening communicating with the second of the regions of the sensing chamber;

wherein the main body includes a plate therein and wherein the reservoir and the main chamber are substantially defined in the plate, wherein the main body includes a longitudinal axis and wherein the regulator, the flow rate selector, and the plate are secured to each other along the longitudinal axis.

12. The apparatus of claim 11, wherein the regulator, the flow rate selector, and the plate are each substantially cylindrical and have central axes mounted coaxially with the longitudinal axis of the main body.

13. The apparatus of claim 11, wherein the main body includes an end cap having inner and outer surfaces, wherein the plate includes a plate surface opposing the inner surface of the end cap to define the sensing chamber, and wherein the delivery outlet is defined in the outer surface of the end cap.

14. The apparatus of claim 11, wherein the regulator, the flow rate selector, and the plate are secured in series.

15.

A pneumatic apparatus for delivering pulses of gas from a gas delivery source through a single-lumen cannula in response to inhalation by a patient, the apparatus comprising:

a main body having an inlet for receiving gas from a gas source, an outlet for delivering the pulses of gas, and a plurality of chambers defined between the inlet and the outlet;

the main body including:

a regulator pneumatically connected to the inlet for producing a delivery pressure for the gas exiting therefrom;

a flow-rate selector secured relative to the regulator so as to receive the gas exiting therefrom, the flow-rate selector having a pressure passage and a variable rate passage extending therethrough, the selector including a plurality of orifices defined therein, the orifices sized to correspond to selected oxygen delivery rates of the apparatus, the selector being movably mounted to position a selected one of the orifices in the variable rate passage to cause the gas to exit from the variable rate passage at a selected oxygen delivery rate;

a reservoir defined within the main body and having a reservoir inlet and a reservoir outlet, the reservoir located within the main body to receive the gas from the variable rate passage;

a main valve located within the main body, the main body comprising a chamber and a movable element received within the chamber, the chamber having a chamber inlet therein, a chamber outlet, and a pressure inlet, the chamber inlet in pneumatic communication with the reservoir outlet, and the pressure inlet in pneumatic communication with the pressure passage of the flow rate selector, the chamber inlet and the pressure inlet disposed in the chamber on opposite sides of the movable element, the movable element being movable to open and close the reservoir outlet;

a sensing valve comprising a sensing chamber with a sensing element received therein and a port defined in the sensing chamber, the sensing element movably mounted to seal the port in response to predetermined pressures in the sensing chamber, the sensing element dividing the sensing chamber into two regions;

a vent to atmosphere defined in the main body and extending between the sensing chamber and the exterior surface of the main body, the vent to atmosphere being in pneumatic communication with the first of the regions of the sensing chambers;

a delivery outlet adapted to connect to the single-lumen cannula;

a delivery passage having a delivery end communicating with the delivery outlet and a chamber end communicating with the chamber outlet, the delivery passage receiving gas from the chamber received from the reservoir;

a sensing passage disposed within the main body, the sensing passage having a first opening communicating with the delivery outlet and the delivery passage, and a second opening communicating with the second of the regions of the sensing chamber;

wherein the main body comprises a substantially cylindrical housing with a longitudinal central axis, the housing being substantially symmetrical about the longitudinal central axis.

16. A pneumatic apparatus for delivering pulses of gas from a gas delivery source through a single-lumen cannula in response to inhalation by a patient, the apparatus comprising:

a main body having an inlet for receiving gas from a gas source, an outlet for delivering the pulses of gas, and a plurality of chambers defined between the inlet and the outlet;

the main body including
  a regulator pneumatically connected to the inlet for producing a delivery pressure for the gas exiting therefrom;

a flow-rate selector secured relative to the regulator so as to receive the gas exiting therefrom, the flow-rate selector having a pressure passage and a variable rate passage extending therethrough, the selector including a plurality of orifices defined therein, the orifices sized to correspond to selected oxygen delivery rates of the apparatus, the selector being movably mounted to position a selected one of the orifices in the variable rate passage to cause the gas to exit from the variable rate passage at a selected oxygen delivery rate;

a reservoir defined within the main body and having a reservoir inlet and a reservoir outlet, the reservoir located within the main body to receive the gas from the variable rate passage;

a main valve located within the main body, the main body comprising a chamber and a movable element received within the chamber, the chamber having a chamber inlet therein, a chamber outlet, and a pressure inlet, the chamber inlet in pneumatic communication with the reservoir outlet, and the pressure inlet in pneumatic communication with the pressure passage of the flow rate selector, the chamber inlet and the pressure inlet disposed in the chamber on opposite sides of the movable element, the movable element being movable to open and close the reservoir outlet;

a sensing valve comprising a sensing chamber with a sensing element received therein and a port defined in the sensing chamber, the sensing element movably mounted to seal the port in response to predetermined pressures in the sensing chamber, the sensing element dividing the sensing chamber into two regions;

a vent to atmosphere defined in the main body and extending between the sensing chamber and the exterior surface of the main body, the vent to atmosphere being in pneumatic communication with the first of the regions of the sensing chambers;

a delivery outlet adapted to connect to the single-lumen cannula;

a delivery passage having a delivery end communicating with the delivery outlet and a chamber end communicating with the chamber outlet, the delivery passage receiving gas from the chamber received from the reservoir;

a sensing passage disposed within the main body, the sensing passage having a first opening communicating with the delivery outlet and the delivery passage, and a second opening communicating with the second of the regions of the sensing chamber;

wherein the movable element of the main valve comprises a piston and the main chamber comprises a cylinder, wherein the piston reciprocates between first and second positions, the first position having the reservoir outlet and the chamber outlet open to deliver gas from the reservoir to the delivery passage, the second position having the reservoir outlet closed to interrupt the flow of gas therefrom.

17. A conserving device for use in delivering gas from a source of gas to a person, the conserving device comprising:

a reservoir for holding a volume of gas for delivery to the person, the reservoir having a reservoir inlet for receiving the gas from the gas source and a reservoir outlet for discharging the gas;

a delivery system in pneumatic communication with the reservoir to open and close the outlet of the reservoir and to dispense gas intermittently from the reservoir to the person; and a sensing system in pneumatic communication with the person to receive gas to detect a pressure drop upon inhalation by the person, the sensing system also in pneumatic communication with the delivery system to cause the delivery system to open the outlet of the reservoir in response to detecting the pressure drop; and a gas control system pneumatically connected to the gas source, to the delivery system, and to the sensing system, the gas control system increasing the pressure in the sensing system when the gas control system receives gas from the delivery system and, in response to the increased pressure in the sensing system, causing the delivery system to close the outlet of the reservoir and interrupt the delivery of gas to the person;

wherein the reservoir is in pneumatic communication with the gas source and is repressurized thereby while the reservoir is closed and depressurized when the reservoir outlet is opened; and wherein the delivery system dispenses a volume of gas from the reservoir at the time the reservoir outlet is opened.

18. The conserving device of claim 17, further comprising a single delivery outlet, the delivery outlet communicating with the delivery passage to delivery gas to the person therethrough and communicating with the sensing system to communicate inhalation by the person to the sensing system.

19. The conserving device of claim 17, further comprising a flow rate selector having an input and an output side, the input side in communication with the gas source and the output side in communication with the reservoir inlet to vary the flow of gas into the reservoir.

20. The conserving device of claim 17, further comprising a regulator for receiving the gas from the gas source and lowering the pressure thereof.

21. The conserving device of claim 17, further comprising means for delivering a pulse of gas having greater volume in response to slower breathing of the person and having lesser volume in response to more rapid breathing of the person.

22. A conserving device for use in delivering gas from a source of gas to a person, the conserving device comprising:

a reservoir for holding a volume of gas for delivery to the person, the reservoir having a reservoir inlet for receiving the gas from the gas source and a reservoir outlet for discharging the gas;

a delivery system in pneumatic communication with the reservoir to open and close the outlet of the reservoir and to dispense gas intermittently from the reservoir to the person; and a sensing system in pneumatic communication with the person to receive gas to detect a pressure drop upon inhalation by the person, the sensing system also in pneumatic communication with the delivery system to cause the delivery system to open the outlet of the reservoir in response to detecting the pressure drop; and a gas control system pneumatically connected to the gas source, to the delivery system, and to the sensing system, the gas control system increasing the pressure in the sensing system when the gas control system receives gas from the delivery system and, in response to the increased pressure in the sensing system, causing the delivery system to close the outlet of the reservoir and interrupt the delivery of gas to the person;

wherein the reservoir is in pneumatic communication with the gas source and is repressurized thereby while the reservoir is closed and depressurized when the reservoir outlet is opened;

wherein the delivery system dispenses a volume of gas from the reservoir at the time the reservoir outlet is opened;

wherein the delivery system comprises a main valve and a delivery passage, the main valve operable to open and close the reservoir outlet, the delivery passage adapted to be in pneumatic communication with the reservoir outlet when the main valve is open and with the person to receive the gas;

wherein the sensing system comprises a sensing valve in a sensing chamber having two regions;

wherein the gas control system comprises a pressure line and a sensing passage, the pressure line in communication with the main valve, and the sensing passage communicating between the delivery passage and the sensing chamber.

23. The conserving device of claim 22, wherein the sensing passage of the gas control system comprises a check valve operable between a first position closing the sensing chamber and a second position to open the sensing chamber.

24. A conserving device for use in delivering gas from a source of gas through a gas line to a patient, the conserving device comprising:

a reservoir having an inlet for receiving the gas into the reservoir and an outlet for discharging the gas from the reservoir;

a main valve in pneumatic communication with the outlet of the reservoir and operable between a closed position for closing the outlet to pressurize the reservoir and an open position for opening the outlet to depressurize the reservoir;

a pressure line extending pneumatically and communicating between the source of gas and the main valve to bias the main valve towards the closed position, the pressure line terminating in a port;

a sensing valve in pneumatic communication with the port and operable between a closed position to close the port and an open position to open the port and allow the gas from the pressure line to flow therethrough;

a delivery outlet in pneumatic communication with the outlet of the reservoir and the gas line to deliver the gas discharged from the reservoir, the delivery outlet in further pneumatic communication with the sensing valve;

a check valve communicating between the delivery outlet and the sensing valve;

wherein the check valve opens in response to inhalation by the patient through the gas line connected to the delivery outlet to permit air to be drawn from the sensing valve to move the sensing valve to the open position to open the port, whereupon the biasing of the main valve is sufficiently reduced for the main valve to move to the open position, whereupon the outlet to the reservoir is opened and the gas therein is discharged from and exits through the delivery outlet to the patient; and wherein the check valve is disposed relative to the delivery outlet so that a portion of the gas flowing into the delivery outlet passes through the check valve to bias the sensing valve toward the closed position.

25. A conserving device for use in delivering gas from a source of gas through a gas line to a patient, the conserving device comprising:

a reservoir having an inlet for receiving the gas into the reservoir and an outlet for discharging the gas from the reservoir;

a main valve in pneumatic communication with the outlet of the reservoir; the main valve having a reciprocable element; and a pressure line extending pneumatically and communicating between the source of gas and the main valve to bias the main valve towards the closed position, the pressure line terminating in a port;

a sensing valve in pneumatic communication with the port and operable between a closed position to close the port and an open position to open the port and allow the gas from the pressure line to flow therethrough;

the reciprocable element of the main valve movable between first and second positions, the first position spaced from the reservoir outlet so that said outlet is open and against the port to seal the pressure line; the second position sealing the reservoir outlet so that gas is not dischargeable therefrom and spaced from the port to open the pressure line;

wherein the movable element comprises first and second sides having corresponding surface areas, the first side being in pneumatic communication with the reservoir outlet, so that pressurized gas in the reservoir acts on the first side, the second side being in pneumatic communication with the pressure line, so that pressurized gas in the pressure line acts on the second side, and wherein, in the first position, the pressurized gas in the reservoir acts upon a larger surface area than is acted upon by the pressurized gas in the pressure line, and, in the second position, pressurized gas in the reservoir acts upon a smaller surface area than is acted upon by the pressurized gas in the pressure line.

26. A method of delivering pulses of gas to a patient through a cannula, the method comprising:

a. providing a housing with a reservoir and a valve located therein in pneumatic communication with a source of gas, the valve having first and second sides with corresponding surface areas;

b. receiving gas from the source of gas into the reservoir;

c. applying gas from the gas source to the surface area of the first side of the valve to close the reservoir with the second side of the valve, the closed reservoir thereby becoming pressurized;

d. applying the pressure in the reservoir over a surface area of the second side of the valve which is smaller than the surface area of the first side to which gas is being applied, whereby the balance of forces exerted on the sides of the valve seals the reservoir;

e. relieving the pressure of the gas applied to the first side of the valve, in response to inhalation by the person, by an amount sufficient to change the balance of forces exerted on the valve and unseal the second side of the valve from the reservoir;

f. upon unsealing of the reservoir, applying the pressurized gas in the reservoir over substantially the entire surface area of the second side to rapidly increase the force exerted on the second side and move the first side of the valve to seal against the source of gas;

g. applying the pressurized gas from the source of gas over a surface area of the first side of the valve which is smaller than the surface area of the second side to which the pressurized gas from the reservoir is being applied, whereby the balance of forces exerted on the sides of the valve seal the first side against the source of gas;

h. delivering at least a portion of the volume of gas stored in the reservoir to the patient, the relatively rapid movement of the valve causing a pulse of oxygen to exit the reservoir, the delivery relieving the pressure applied to the second side sufficient to change the balance of forces exerted on the valve and unseal the first side from the source of gas;

i. upon unsealing of the source of gas, applying the pressurized gas from the source of gas over substantially the entire surface area of the first side to rapidly increase the force exerted on the first side and reciprocate the valve back to its initial position with the second side of the valve sealed against the reservoir;

j. performing steps e through i in response to each inhalation by the person to delivery pulses of oxygen on demand.

27. The method of claim 26, wherein steps e through i occur within the first second after inhalation by the person.

* * * * *